US007256301B2

(12) United States Patent  
Erguen et al.

(10) Patent No.: US 7,256,301 B2
(45) Date of Patent: Aug. 14, 2007

(54) METHOD AND SYSTEM FOR THE ESTERIFICATION OF FATTY ACIDS

(75) Inventors: Nurhan Erguen, Vienna (AT); Peter Panning, Poettsching (AT)

(73) Assignee: ENERGEA Umwelttechnologie GmbH, Klosterneuburg (AT)

( * ) Notice: Subject to any disclaimer, the term of this patent is extended or adjusted under 35 U.S.C. 154(b) by 0 days.

(21) Appl. No.: 10/961,031

(22) Filed: Oct. 12, 2004

(65) Prior Publication Data

US 2005/0065357 A1    Mar. 24, 2005

Related U.S. Application Data

(63) Continuation of application No. PCT/AT03/00101, filed on Apr. 7, 2003.

(30) Foreign Application Priority Data

Apr. 12, 2002    (AT) ................ A 569/2002

(51) Int. Cl.
 *C11C 3/00* (2006.01)
 *C11C 1/00* (2006.01)
(52) U.S. Cl. .................................... 554/167
(58) Field of Classification Search ........... 554/167
 See application file for complete search history.

(56) References Cited

U.S. PATENT DOCUMENTS

| 2,543,055 | A | 2/1951 | Pool et al. |
| 2,583,206 | A | 1/1952 | Borck et al. |
| 3,614,069 | A | 10/1971 | Murry |
| 4,164,506 | A | 8/1979 | Kawahara et al. |
| 4,275,012 | A | 6/1981 | Kokubo et al. |
| 4,608,202 | A | 8/1986 | Lepper et al. |
| 4,652,406 | A | 3/1987 | Lepper et al. |
| 4,655,879 | A | 4/1987 | Brockmann et al. |
| 4,698,186 | A | 10/1987 | Jeromin et al. |

(Continued)

FOREIGN PATENT DOCUMENTS

DE    3501761    7/1986

(Continued)

OTHER PUBLICATIONS

Database WPI, Section Ch, Week 199818, Derwent Publications Ltd., London, GB; Class E19, AN 1998-200910, XP002251804.

(Continued)

*Primary Examiner*—Deborah D. Carr
(74) *Attorney, Agent, or Firm*—Greenblum & Bernstein, P.L.C.

(57) ABSTRACT

Method and apparatus for esterification of fatty acids or fatty acids contained in fats and oils with lower monovalent alcohol having 1 to 4 carbon atoms, comprising combining in a reaction section the fatty acids or fatty acids contained in fats and oils, and the alcohol to form a mixture, the combining forming enlarged interphases of the mixture by high or powerful dynamic shear forces and turbulence; at least one of strong mineral acid and acid ion exchange resin being present in the reaction section or a post-reaction section; starting esterification in the reaction section under pressure of 2 to 500 bar, and reducing pressure during the esterification so that a high interphase is maintained; and the esterification is carried out in the reaction section at a temperature of 50 to 300° C.

19 Claims, 1 Drawing Sheet

U.S. PATENT DOCUMENTS

| | | |
|---|---|---|
| 5,324,853 A | 6/1994 | Jones et al. |
| 5,388,905 A | 2/1995 | Ake et al. |
| 5,399,731 A | 3/1995 | Wimmer |
| 5,424,467 A | 6/1995 | Bam et al. |
| 5,482,633 A | 1/1996 | Muraldihara et al. |
| 5,514,820 A | 5/1996 | Assmann et al. |
| 5,536,856 A | 7/1996 | Harrison et al. |
| 5,645,696 A | 7/1997 | Woo et al. |
| 5,773,636 A | 6/1998 | Demmering et al. |
| 5,849,939 A | 12/1998 | Mittelbach et al. |
| 5,945,529 A | 8/1999 | Corrigan et al. |
| 6,015,440 A | 1/2000 | Noureddini |
| 6,440,057 B1 | 8/2002 | Ergün et al. |
| 2002/0013486 A1 | 1/2002 | Ergun et al. |

FOREIGN PATENT DOCUMENTS

| | | |
|---|---|---|
| DE | 4338111 | 5/1995 |
| EP | 0127104 | 12/1984 |
| EP | 0184740 | 6/1986 |
| EP | 0535290 | 11/1994 |
| EP | 0708813 | 12/1996 |
| EP | 0713857 | 1/1999 |
| GB | 2169895 | 7/1986 |
| JP | 10-52634 | 2/1998 |
| WO | 90/08127 | * 7/1990 |
| WO | 95/02661 | 1/1995 |
| WO | 99/26913 | 6/1999 |
| WO | 02/38529 | 5/2002 |
| WO | 03/087278 | 10/2003 |

OTHER PUBLICATIONS

"Organikum", 13$^{th}$ Ed., 1974, pp. 441.

Weygand/Hilgetag, "Organisch-Chemische Experimentierkunst", 4$^{th}$ Ed., 1970, pp. 377 et seq.

Chemical Abstracts, vol. 118, Mar. 15-19, Abstracts 93625-125087, pp. 202.

"Use of Ultrasound Radiation in Organic Synthesis," Guanxi Chemical Industry, vol. 28, No. 2, Jun. 1999 (in Chinese).

* cited by examiner

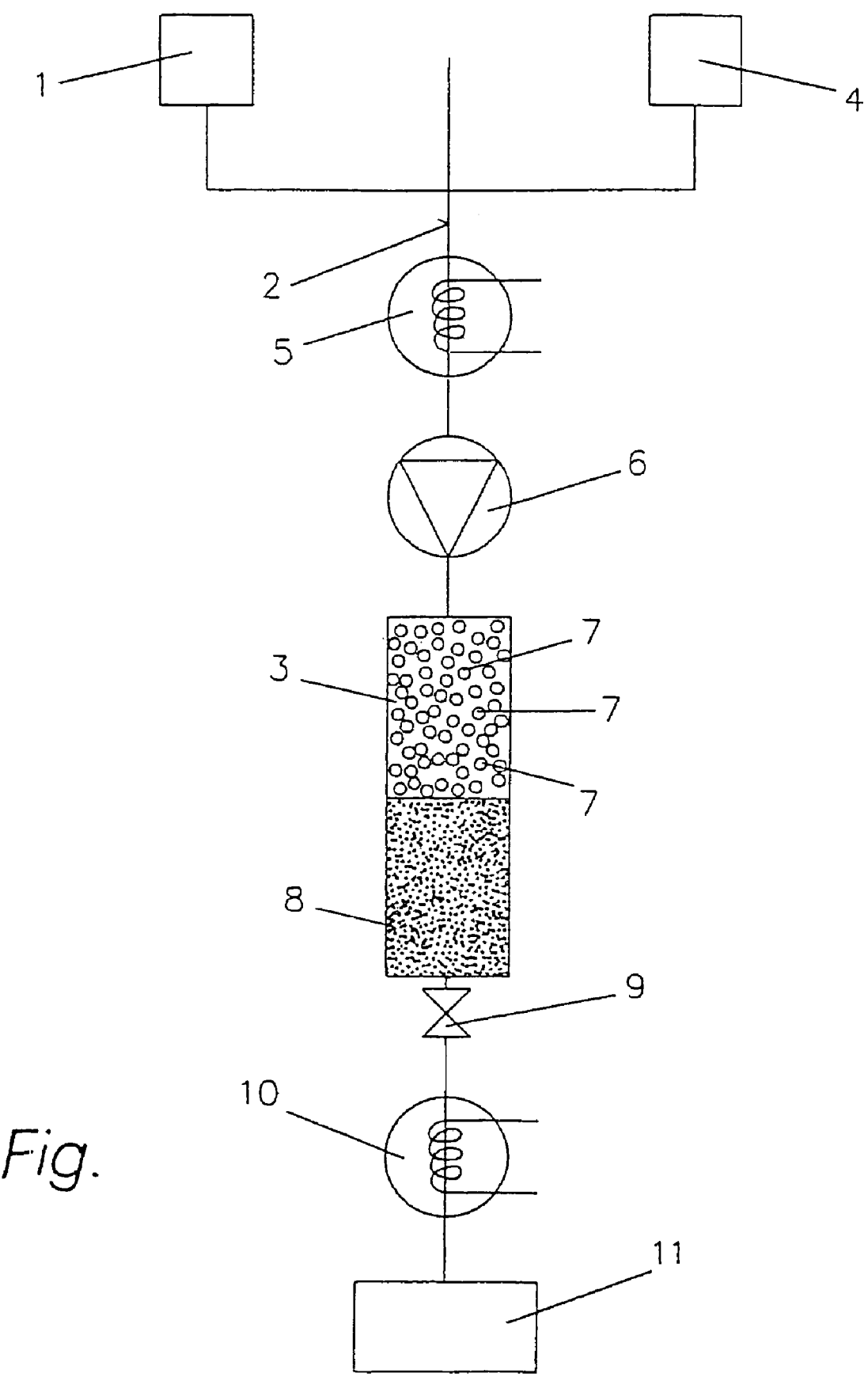
Fig.

METHOD AND SYSTEM FOR THE ESTERIFICATION OF FATTY ACIDS

CROSS-REFERENCE TO RELATED APPLICATIONS

The present application is a Continuation of International Patent Application No. PCT/AT03/00101 filed Apr. 7, 2003 and claims priority under 35 U.S.C. §119 of Austria Patent Application No. A 569/2002, filed Apr. 12, 2002. Moreover, the disclosure of International Patent Application No. PCT/AT03/00101 is expressly incorporated by reference herein in its entirety.

BACKGROUND OF THE INVENTION

1. Field of the Invention

The present invention relates to a method for the esterification of fatty acids and/or fatty acids contained in fats and oils with lower monovalent alcohols, especially methanol, whereby the fatty acids with strong mineral acids, such as sulphuric acid, dissolved in lower alcohols, especially in methanol and/or exclusively in the lower alcohols, especially in methanol, are compounded with acid ion exchanger resins. Furthermore, the invention relates to a system for the implementation of the method.

2. Discussion of Background Information

From textbooks for organic-preparatory chemistry, such as "Organikum", 13th ed., 1974 page 441 et seq. or Weygand/Hilgetag, „Organisch-Chemische Experimentierkunst, 4th ed., 1970, page 377 et seq., it is known that carboxylic acid esters or fatty acid esters may be esterified by esterification of the free acids with lower alcohols, preferably at the temperature of ebullition of the alcohols in presence of strong acids, such as hydrogen chloride, sulphuric acid or sulphonic acids.

A method for the esterification of a fatty acid/fatty acid ester mixture, isolated from the "glycerine phase", is described in EP 708 813 A, whereby the free fatty acids obtained from the neutralization of the "glycerine phase" are heated to a temperature of 85° C. for two hours, with methanol and concentrated sulphuric acid acting as a catalyst, whereby the content of free fatty acids decreases from about 50% to 12.5% and the entire mixture is supplied without any further treatment to an alkali-catalyzed transesterification and the catalyst acid is exported through the transesterification process.

Further methods for esterification of free fatty acids are described in EP 127 104 A, EP 184 740 A and U.S. Pat. No. 4,164,506, whereby the free fatty acids are present in a mixture with fatty acid triglycerides and the esterification is carried out by heating with methanol at 65° C., whereby sulphuric acid or a sulphonic acid act as a catalyst.

Furthermore, a method and a device for the production of carboxylic acid ester are known from WO 90/08127 A, whereby the esterification is carried out in a counterflow reaction column. The carboxylic acid to be esterified is introduced into the counterflow reaction column from above and alcohol, in particular methanol, is introduced from below in vapour form. The mixture is practically circulated for esterification. Several plates with ion exchangers are arranged in the column, the carboxylic acid reacts with the alcohol in the esterification zones. The water which is produced during esterification is removed with the methanol vapour during the esterification process at the upper end of the column, while the ester is removed at the lower end of the column.

Moreover, a method for the catalytic or non-catalytic esterification of acids is known from U.S. Pat. No. 5,324,853. In the course of the method, the reaction mixture is heated in a container with several stirring devices, so that the water that is produced is removed in vapour form during the esterification process.

In U.S. Pat. No. 5,945,529, a transesterification process based on the counterflow principle and using an inert gas is described. In the method, the lower alcohol that is produced during the transesterification is removed by a strip gas during the process. The transesterification is carried out by a multistage column or a multistage counterflow reactor.

An esterification of unsaturated carboxylic acids is known from EP 0 713 857 A1. Here, the water, produced by the esterification, is extracted from the various esterification zones containing ion exchangers during the process with the help of a medium in vapour form. During the process, the vapours are withdrawn and the reaction water is removed from the cycle. The reaction vessel that is used for such purpose has a fixed bed with 1 to 10 stages. Each stage is comprised of a filter- and catalyst bed.

From the citation index of the WPI database, section Ch, week 199818, XP 00251804 a horizontal tank with stirring devices is known, wherein vapour is withdrawn during the process in order to extract water that is produced.

In conclusion, WO 02/38529 A is referred to. In this publication, a method for the production of fatty acid esters of lower alcohols is described, wherein by neutralization of the glycerine phase and by a subsequent esterification with an acid, a diesel substitute fuel is produced.

The serious disadvantage of all these known methods lies in the fact, however, that the esterification step requires an enormous amount of time. Thus, as a rule the kind of esterification requires stirring over a period of two to three hours.

SUMMARY OF THE INVENTION

The present invention provides a method of the above-mentioned type which allows a rational production in an economically acceptable system, preferably in an industrial-sized system, but is also economic in small systems.

The present invention provides a method for esterification of at least one of fatty acids or fatty acids contained in fats and oils with lower monovalent alcohol having 1 to 4 carbon atoms, comprising combining in a reaction section the at least one of fatty acids or fatty acids contained in fats and oils, and the lower monovalent alcohol to form a mixture, the combining forming enlarged interphases of the mixture by at least one of high or powerful dynamic shear forces and turbulence; at least one of strong mineral acid and acid ion exchange resin being present in the reaction section or a post-reaction section; and starting esterification in the reaction section under pressure of 2 to 500 bar, and reducing pressure during the esterification so that a high interphase is maintained; and the esterification is carried out in the reaction section at a temperature of 50 to 300° C.

The present invention also provides a system for esterification of at least one of fatty acids or fatty acids contained in fats and oils with lower monovalent alcohol having 1 to 4 carbon atoms, comprising a reaction section capable of combining at least one of fatty acids or fatty acids contained in fats and oils, and lower monovalent alcohol to form a mixture, the combining forming enlarged interphases of the mixture by at least one of high or powerful dynamic shear forces and turbulence, the reaction section being constructed and arranged to obtain esterification of the at least one of fatty acids or fatty acids contained in fats and oils with the alcohol; the reaction section comprising a pipe filled with mechanical devices providing high shearing forces and powerful dynamic turbulence in the reaction section, such as at least one of balls, baffles and blades; and a pump introducing liquid into the reaction section at a high pressure.

A strong mineral acid, such as sulphuric acid, can be added to the reaction section. The strong mineral acid can comprise sulphuric acid.

The alcohol can be methanol.

The starting pressure can 50 to 200 bar, and particularly 70 to 150 bar.

The temperature can be 80 to 150° C.

An acid ion exchange resin can be included in a post-reaction section.

High shearing forces and powerful dynamic turbulence can be produced by mechanical devices included in the reaction section.

The enlarged interphase can be created by ultrasound.

A non-turbulent post-reaction section can follow the reaction section.

The pressure from the reaction section can be maintained in the post-reaction section.

The pressure from the reaction section can be maintained at the initial pressure of the reaction section in the post-reaction section.

The pressure from the reaction section can be reduced from the initial pressure of the reaction section in the post-reaction section.

The post-reaction section can be filled with strong-acid ion exchangers.

The pump can comprise a high-pressure pump. The high pressure pump can be capable of providing a pressure in the reaction section of 2 to 500 bar, particularly, 50 to 200 bar, and more particularly 70 to 150 bar.

The reaction section can comprise a pipe filled with balls. The balls can be of the same or different sizes.

A heater can precede the reaction section.

A cooler can follow the reaction section or the post-reaction section.

The method according to the invention provides, in a reaction section, that interphases and boundary surfaces, respectively, of the mixture are increased by high or powerful dynamic shearing forces and/or turbulence, whereby the esterification starts under pressure, whereby the pressure at the beginning of the reaction section lies at 2 to 500 bar, in particular at 50 to 200 bar, and most preferably between 70 and 150 bar, and the pressure is reduced during the esterification, whereby the pressure loss maintains a high interphase, and in that the reaction is carried out in the reaction section at a temperature of 50 to 300° C., in particular at 80 to 150° C.

The present invention allows for the first time to provide a pre-product for the production of bio-diesel by base-catalyzed. transesterification. Thus, the possibility is provided to produce diesel fuel, so-called eco-diesel or bio-diesel, in ecologically optimal conditions of production while maintaining all the advantages thereof. With this invention positive economic and ecological arguments are provided, which will stimulate a more intensive discourse on the role of renewable energy and resources.

Another surprising advantage results from the invention, namely in the field of waste management or hazardous waste disposal. With this invention it is also possible to recycle and reuse used table oil ecologically, even if the oil has a high content of fatty acids. The use of used table oil in the method according to the invention is possible without reservations due to the high purity of the end products.

The present invention makes it possible to accelerate the reaction through the enlargement of the interphases and through dynamic processes during the esterification. Due to the high or powerful dynamic turbulence, the size of the drops in the liquid phases is effectively reduced, so that much smaller drops are produced, resulting in a much larger surface, which means that the chemical balance state is reached faster. Reaching the chemical balance state may take less than a minute. This means an enormous shortening of the reaction time. However, the method according to this invention is not suited for the so-called sedimentation method, since the sedimentation times would be too long due to the fine distribution of the drops.

Another advantage lies in the fact that the methanol remains liquid due to the high pressure. Furthermore, the high reaction rate is advantageously achieved as a consequence of the high temperature.

According to an embodiment of the invention, the high shear forces or powerful dynamic turbulence are produced by mechanical devices in the reaction section. The type of devices is easy to install and therefore does not require much maintenance during operation. The turbulence is created primarily by the rapid flow of the mixture around the devices. Moreover, such a reactor is inexpensive and extremely compact.

According to another embodiment of the invention, the large interphases are created by ultrasound. The integration of an ultrasound device has proven to be advantageous, since the esterification can therewith be specifically accelerated through large interphases.

According to another special feature of the invention, the reaction section is followed by a non-turbulent post-reaction section. By the residence time of the reaction mixture in the post-reaction section, an increase of the esterification degree is obtained.

According to one embodiment of the invention, in the post-reaction section a pressure, preferably the initial pressure of the reaction section, is maintained or possibly further reduced. Maintaining the pressure also contributes to the improvement of the esterification degree. According to specific parameters in the esterification process, however, a further reduction of pressure may also be of advantage.

According to a special further development of the invention, the post-reaction section is filled with strong-acid ion exchangers. In a process implementation with ion exchangers, the compounding of the fats with acids is omitted in a known manner. Also by the process, an optimal esterification process is achieved.

The present invention also provides a system for the implementation of the method.

The system according to the invention is characterized in that the reaction section is a pipe filled with balls of the same size or different sizes and/or possibly has devices such as baffles, propellers (blades) or the like, whereby a pump, in particular a high-pressure pump, is provided for the introduction of the liquid into the reaction section. The advantageous turbulence is created primarily by the rapid flow of the mixture around the balls and/or devices. The integration of a high-pressure pump has proven to be advantageous because the turbulence achieves high dynamics and thus a large interphase for the esterification.

In accordance with another embodiment of the invention, an ultrasound device is provided in the reaction section. The integration of an ultrasound device has proven advantageous, since the esterification can therewith be specifically accelerated through large interphases.

According to a further embodiment of the invention, the reaction section is preceded by a heater, and a cooler possibly follows the reaction section or the post-reaction section. By the heater, the reaction mixture can be brought to the desired high temperature and can be cooled down with the cooler according to the parameters for the process.

BRIEF DESCRIPTION OF THE DRAWINGS

The invention will now be explained in more detail based on an embodiment which is illustrated in the drawing.

The sole FIGURE schematically shows a system for the implementation of the method for the esterification of fatty acids.

DETAILED DESCRIPTION OF THE INVENTION

According to the FIGURE, the raw material, such as higher, saturated and/or unsaturated fats of vegetable and/or animal origin, containing free fatty acids, flows into a supply line 2 from container 1 leading to a reaction section 3. The method is particularly suitable for fats having a higher or high content, preferably more than 5%, of free fatty acids. The method may, for example, be used with the production of fatty acid methyl ester, whereby a high profitability can be guaranteed.

Naturally, the method may also be used with pure fatty acids.

From the container 4, the lower alcohol, in particular methanol, is pumped together with the acid, in particular sulphuric acid, into the supply line 2 leading to the reaction section 3.

The reaction mixture 3 is brought to the corresponding temperature by a heater 5 which is arranged before the reaction section 3. The reaction in the reaction section 3 is carried out at a temperature of 50 to 300° C., in particular at a temperature of 80 to 150° C.

The heated reaction mixture is introduced into the reaction section 3 via a high-pressure pump 6. In the reaction section 3 the reaction mixture is exposed to high shear forces, whereby powerful dynamic turbulence is produced. This results in the interphases of the reaction mixture becoming immensely enlarged. The high shearing forces and the powerful dynamic turbulence respectively are created by mechanical devices in the reaction section 3.

The mechanical devices in the reaction section 3 may be balls 7 of the same size or different sizes. However, it is also possible to provide, possibly in addition, devices such as baffles, propellers (blades) or the like.

The enlargement of the interphases of the reaction mixture may also be achieved by an ultrasound device. Of course, the device may also be provided in addition to the mechanical devices.

Due to the high and powerful dynamic turbulence respectively, the size of the drops in the liquid phases is effectively reduced, so that much smaller drops are produced, resulting in a much larger surface, whereby the chemical balance state is reached faster. Reaching the chemical balance state may take less than a minute. This provides enormous shortening of the reaction time.

In the reaction section 3, part of the pressure that is present at the beginning of the reaction section 3 is reduced.

In order to increase the esterification degree, the reaction section 3 may be followed by a non-turbulent post-reaction section 8 which, possibly under the initial pressure of the reaction section 3, calms down the reaction mixture. For this purpose, the post-reaction section 8 is provided with a pressure keeping valve 9 at its end. If this should prove to be more advantageous for the procedure of the process, however, pressure may also be reduced in the post-reaction section 8.

According to an alternative procedure of the process without the addition of acid, in particular sulphuric acid, at the beginning of the reaction section 3, a strong-acid ion exchanger, in particular an ion exchanger resin, is provided in the post-reaction section 8.

The post-reaction section 8 is followed by a cooler 10 which cools down the reaction mixture correspondingly, before it is collected in a container 11 for further processing.

In conclusion, it must be pointed out that for better legibility the individual components and assemblies in the drawing are not shown proportionally or to scale.

What is claimed is:

1. A method for esterification of fatty acids with lower monovalent alcohol having 1 to 4 carbon atoms, comprising:
   combining in a reaction section the fatty acids and the lower monovalent alcohol to form a mixture, the combining forming enlarged interphases of the mixture by at least one of high or powerful dynamic shear forces and turbulence;
   at least one of strong mineral acid and acid ion exchange resin being present in the reaction section or a post-reaction section;
   starting esterification in the reaction section under pressure of 2 to 500 bar, and reducing pressure during the esterification so that a high interphase is maintained; and
   the esterification is carried out in the reaction section at a temperature of 50 to 300° C.

2. The method according to claim 1, comprising adding a strong mineral acid to the reaction section, the strong mineral acid comprising sulphuric acid and the alcohol comprising methanol.

3. The method according to claim 1, wherein the alcohol is methanol.

4. The method according to claim 1, wherein the starting pressure is 50 to 200 bar.

5. The method according to claim 1, wherein the starting pressure is 70 to 150 bar.

6. The method according to claim 1, wherein the temperature is 80 to 150° C.

7. The method according to claim 1, wherein the strong mineral acid comprises sulphuric acid.

8. The method according to claim 1, comprising adding strong mineral acid to said reaction section.

9. The method according to claim 8, wherein the strong mineral acid comprises sulphuric acid.

10. The method according to claim 1, comprising including an acid ion exchange resin in a post reaction section.

11. The method according to claim 10, comprising adding strong mineral acid to the reaction section.

12. The method according to claim 1, wherein high shearing forces and powerful dynamic turbulence are produced by mechanical devices included in the reaction section.

13. The method according to claim 1, wherein the enlarged interphase is created by ultrasound.

14. The method according to claim 1, comprising a non-turbulent post-reaction section following the reaction section.

15. The method according to claim 14, wherein pressure from the reaction section is maintained in the post-reaction section.

16. The method according to claim 15, wherein pressure from the reaction section is maintained at the initial pressure of the reaction section in the post-reaction section.

17. The method according to claim 14, wherein pressure from the reaction section is reduced from the initial pressure of the reaction section in the post-reaction section.

18. The method according to claim 1, wherein the post-reaction section is filled with strong-acid ion exchangers.

19. The method of claim 1 wherein the fatty acids comprise fatty acids contained in fats and oils.

* * * * *